(12) United States Patent
Yang et al.

(10) Patent No.: US 8,406,375 B2
(45) Date of Patent: *Mar. 26, 2013

(54) ARTICLE INSPECTION DEVICE AND INSPECTION METHOD

(75) Inventors: Yigang Yang, Beijing (CN); Tiezhu Li, Beijing (CN); Qinjiar Zhang, Beijing (CN); Yi Zhang, Beijing (CN); Yingkang Jin, Beijing (CN); Qinghao Chen, Beijing (CN); Yuanjing Li, Beijing (CN); Yinong Liu, Beijing (CN)

(73) Assignees: Tsinghua University, Beijing (CN); Nuctech Company Limited, Beijing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 13/142,712

(22) PCT Filed: Dec. 28, 2010

(86) PCT No.: PCT/CN2010/080369
§ 371 (c)(1),
(2), (4) Date: Jun. 29, 2011

(87) PCT Pub. No.: WO2012/000298
PCT Pub. Date: Jan. 5, 2012

(65) Prior Publication Data
US 2012/0207271 A1    Aug. 16, 2012

(30) Foreign Application Priority Data
Jun. 30, 2010    (CN) .......................... 2010 1 0223292

(51) Int. Cl.
*G01N 23/201*    (2006.01)
(52) U.S. Cl. .......................................... 378/87; 378/62
(58) Field of Classification Search ............... 378/86, 378/87, 62, 88, 89, 90
See application file for complete search history.

(56) References Cited

U.S. PATENT DOCUMENTS

| | | | |
|---|---|---|---|
| 7,078,699 B2 * | 7/2006 | Seppi | 378/50 |
| 2009/0168958 A1 | 7/2009 | Cozzini et al. | 378/57 |
| 2012/0002788 A1 * | 1/2012 | Yang et al. | 378/88 |

FOREIGN PATENT DOCUMENTS

| | | |
|---|---|---|
| CA | 1 135 878 | 11/1982 |
| CN | 1343883 | 4/2002 |

(Continued)

OTHER PUBLICATIONS

Search Report and Written Opinion from corresponding application PCT/CN2010/080369, dated Mar. 31, 2011, 6 pgs.

(Continued)

*Primary Examiner* — Glen Kao
(74) *Attorney, Agent, or Firm* — Westman, Champlin & Kelly, P.A.

(57) ABSTRACT

The present invention discloses an article inspection device, comprising: an x-ray machine, a collimation unit, a transmission detector array and a scattering detector array. The scattering detector array comprising a plurality of same scattering detector modules arranged in a matrix of i-rows and j-columns. A transmission cross section of the article transmitted by the x-rays is divided into a plurality of same sub-regions arranged in a matrix of i-rows and j-columns. The plurality of scattering detector modules arranged in i-rows and j-columns correspond to the plurality of sub-regions arranged in i-rows and j-columns one by one for detecting pair production effect annihilation photons and Compton-effect scattering photons from the respective sub-regions. Obtaining atomic numbers of the respective sub-regions based on a ratio of the pair production effect annihilation photon count to the Compton-effect scattering photon count, so as to form a three-dimensional image of the article. In addition, the present invention further discloses an article inspection method.

13 Claims, 6 Drawing Sheets

FOREIGN PATENT DOCUMENTS

| | | |
|---|---|---|
| CN | 1356540 | 7/2002 |
| CN | 1875264 A | 12/2006 |
| CN | 101629917 | 1/2010 |
| SU | 707403 B * | 6/1981 |
| WO | WO2007054837 | 5/2007 |

OTHER PUBLICATIONS

"The γ Ray Attenuation and Scattering in the Coal and the Correction of Neutron Induced Prompt γ Spectra", by Y. Yang et al., *Nuclear Electronics & Detection Technology*, vol. 23, No. 2, Mar. 2003, pp. 142-146 including translation of Abstract.

Office Action from corresponding Chinese Application No. 201010223292.7, dated Jul. 20, 2012.

Search Report and Written Opinion from Application No. PCT/CN2010/080424, dated Apr. 21, 2011, 6 pages.

\* cited by examiner

ARTICLE INSPECTION DEVICE AND INSPECTION METHOD

CROSS-REFERENCE TO RELATED APPLICATION

This Application is a Section 371 National Stage Application of International Application No. PCT/CN2010/080369, filed Dec. 28, 2010, not yet published, which claims the benefit of Chinese Patent Application No. 201010223292.7 filed on Jun. 30, 2010 in the State Intellectual Property Office of China, the whole content/disclosures of which are incorporated herein by reference.

BACKGROUND OF THE INVENTION

1. Field of the Invention

The present invention relates to an article inspection device for inspecting dangerous goods, such as explosive materials, chemicals, biological weapons, nuclear materials and drugs, hidden in an article. In addition, the present invention also relates to an article inspection method.

2. Description of the Related Art

In order to detect dangerous goods, such as explosives, chemicals, biological weapons, nuclear materials and drugs, hidden in a ship container or in an air container, many technical solutions have been proposed, for example, two popular solutions of which are an x-ray inspection technology and a neutron inspection technology, which are simply described as follows:

1. The X-Ray Inspection Technology a) X-Ray Transmission Solution

The conventional x-ray transmission solution includes a monoenergetic x-ray transmission method and a polyenergetic x-ray transmission method. In each of the methods attenuation information of x-rays transmitting through an article to be inspected is firstly detected by use of a transmission detector array, and then a two-dimensional image of the article is formed based on the attenuation information. The two-dimensional image is representative of mass thickness information of the article along the x-rays transmission path. In this way, by analyzing the shape of the two-dimensional image, an operator can determine whether the article contains dangerous goods therein. However, the x-ray transmission solution can only obtain an integration of attenuation ability of the article to be inspected along the x-rays transmission path, thereby it can not discriminate a thinner article having a high atomic number and a high atomic density from a thicker article having a low atomic number and a low atomic density. Therefore, it can not detect nuclear materials hidden in the article with enough accuracy.

b) Nuclear Resonance Fluorescence Solution

The conventional nuclear resonance fluorescence solution comprises firstly adopting x-rays to excite an atomic nucleus, and then detecting gamma photons generated by the atomic nucleus after being excited. In this way, the conventional nuclear resonance fluorescence solution can obtain "fingerprint information" of the atomic nucleus of interest. However, the x-rays that can generate resonance absorption have a very small energy spectrum width, which causes the article to generate a few number of resonance fluorescence but a great number of scattering photons after being irradiated by the x-rays, thereby the conventional nuclear resonance fluorescence solution is disadvantageously interfered by background information from the scattering photons, and has a poor detection sensitivity. For the purpose of improving the detection sensitivity, another new method of using an adjustable monoenergetic x-ray source is recently proposed, but it needs an electron accelerator with energy of more than 100 MeV.

2. The Neutron Inspection Technology a) Neutron Transmission Solution

The conventional neutron transmission solution is similar with the above conventional x-ray transmission solution. The neutron is sensitive to materials having a low atomic number, particularly hydrogen, but usually is not sensitive to those having a high atomic number. Thereby, compared with the above conventional x-ray transmission solution, the conventional neutron transmission solution is good at detecting materials containing a great deal of hydrogen. However, the neutron transmission solution also can only obtain integration information along the neutron transmission path, thereby it can not discriminate chemical elements of materials arranged at various spatial locations. Therefore, it can not detect nuclear materials hidden in the article, either.

b) Elements Concentration Analysis Solution

The elements concentration analysis solution can discriminate different elements based on gamma rays induced by reaction of neutrons with nuclear. Furthermore, another elements concentration analysis solution that can discriminate different elements arranged in three-dimensional space is recently proposed, wherein a three-dimensional space element image of an article to be inspected, such as a container or a vehicle, can be formed in a 5 cm×5 cm×5 cm spatial resolution. However, the elements concentration analysis solution can only be adapted to nuclides having a large neutron reaction cross section, such as Nitrogen, Carbon, Oxygen and Hydrogen, and can not be adapted to nuclear elements having a small neutron reaction cross section. In addition, in the elements concentration analysis solution, it needs to detect energy spectra of $\gamma$-rays with high temporal and energy resolution. Because of the very complicated $\gamma$-rays spectra induced by the neutron reactions with matter, it is very hard to interpret spectra and extract elements concentration information. Also, the neutron generator should produce neutron pulse of nanosecond width, this is very difficult.

In addition to the above two conventional inspection methods, there are a few of other methods, for example, a nuclear quadrupole resonance (NQR) solution. The NQR method is sensitive to a molecule and can get "fingerprint" information of the molecule. But a condition must be satisfied that the molecule must contain a nucleus whose quadrupole moment is not zero and an electric field gradient in which the atomic nucleus is located must be rather large. However, only a few of materials can satisfy with the above condition. Furthermore, NOR does not work well if the inspected object is electromagnetically shielded.

SUMMARY OF THE INVENTION

The present invention has been made to overcome or alleviate at least one aspect of the above mentioned disadvantages.

Accordingly, it is an object of the present invention to provide an article inspection device and an inspection method that can easily form a three-dimensional image for the article.

According to an aspect of the present invention, there is provided an article inspection device, comprising:

a x-ray machine;

a collimation unit for shaping x-rays generated by the x-ray machine into a sector beam to project an article;

a transmission detector array for detecting the x-rays transmitting through the article so as to form a two-dimensional image of the article; and a scattering detector array comprising a plurality of same scattering detector modules arranged in a matrix of i-rows and j-columns, wherein a transmission cross section of the article transmitted by the x-rays is divided into a plurality of same sub-regions arranged in a matrix of i-rows and j-columns, wherein the plurality of scattering detector modules arranged in i-rows and j-columns correspond to the plurality of sub-regions arranged in i-rows and j-columns one by one for detecting pair production effect annihilation photons and Compton-effect scattering photons from the respective sub-regions produced by the x-rays, wherein obtaining atomic numbers of the respective sub-regions based on a ratio of the pair production effect annihilation photon count to the Compton-effect scattering photon count, so as to form a three-dimensional image of the article, wherein 'i' is a positive integer equal to or greater than 2, and 'j' is a positive integer equal to or greater than 2.

In an exemplary embodiment according to the present invention, each of the scattering detector modules comprises:
a detector; and
a collimator for absorbing the pair production effect annihilation photons and the Compton-effect scattering photons from other sub-regions not corresponding to the collimator to permit only the pair production effect annihilation photons and the Compton-effect scattering photons from the one sub-region corresponding to the collimator to enter the detector.

In an exemplary embodiment according to the present invention, the detector is a LaBr$_3$(Ce) detector, a LaCl$_3$(Ce) detector, a HPGe detector or a CdZnTe detector.

In an exemplary embodiment according to the present invention, the collimator is made of lead, steel or copper.

In an exemplary embodiment according to the present invention, each of the scattering detector modules further comprises: a shield for preventing the pair production effect annihilation photons and the Compton-effect scattering photons, from sub-regions not corresponding to the collimator of the scattering detector module, from entering the detector. In an exemplary embodiment according to the present invention, the shield is made of lead, steel or copper.

In an exemplary embodiment according to the present invention, each of the scattering detector modules further comprises: a hardenite for decreasing the intensity of the pair production effect annihilation photons and the Compton-effect scattering photons from the one sub-region corresponding to the collimator of the scattering detector module. In an exemplary embodiment according to the present invention, the hardenite is made of lead, steel or copper.

In an exemplary embodiment according to the present invention, the detector is located in a collimation slit of the collimator; the shield is disposed at one side of the collimator opposite to the article, and seals an opening of the collimation slit at the one side; and the hardenite is disposed at the other side of the collimator facing the article, and seals the other opening of the collimation slit at the other side.

In an exemplary embodiment according to the present invention, the shield and the collimator are formed into a piece.

In an exemplary embodiment according to the present invention, the x-ray machine is a monoenergetic x-ray machine or a polyenergetic x-ray machine.

In an exemplary embodiment according to the present invention, the x-rays generated by the x-ray machine have energy of more than 1.022 MeV.

According to another aspect of the present invention, there is provided a method for inspecting an article by using article inspection device according to the above, comprising:

detecting an attenuation information of x-rays transmitting through an article by use of a transmission detector array, and detecting pair production effect annihilation photon count and Compton-effect scattering photon count during the x-rays transmitting through the article by use of scattering detector array; and forming a two-dimensional image of the article based on the detected attenuation information, and forming a three-dimensional image of the article based on a ratio of the pair production effect annihilation photon count to the Compton-effect scattering photon count.

BRIEF DESCRIPTION OF THE DRAWINGS

These and/or other aspects and advantages of the invention will become apparent and more readily appreciated from the following description of the embodiments, taken in conjunction with the accompanying drawings, in which.

DETAILED DESCRIPTION OF PREFERRED EMBODIMENTS OF THE INVENTION

Exemplary embodiments of the present disclosure will be described hereinafter in detail with reference to the attached drawings, wherein the like reference numerals refer to the like elements. The present disclosure may, however, be embodied in many different forms and should not be construed as being limited to the embodiment set forth herein; rather, these embodiments are provided so that the present disclosure will be thorough and complete, and will fully convey the concept of the disclosure to those skilled in the art.

Figure 1:
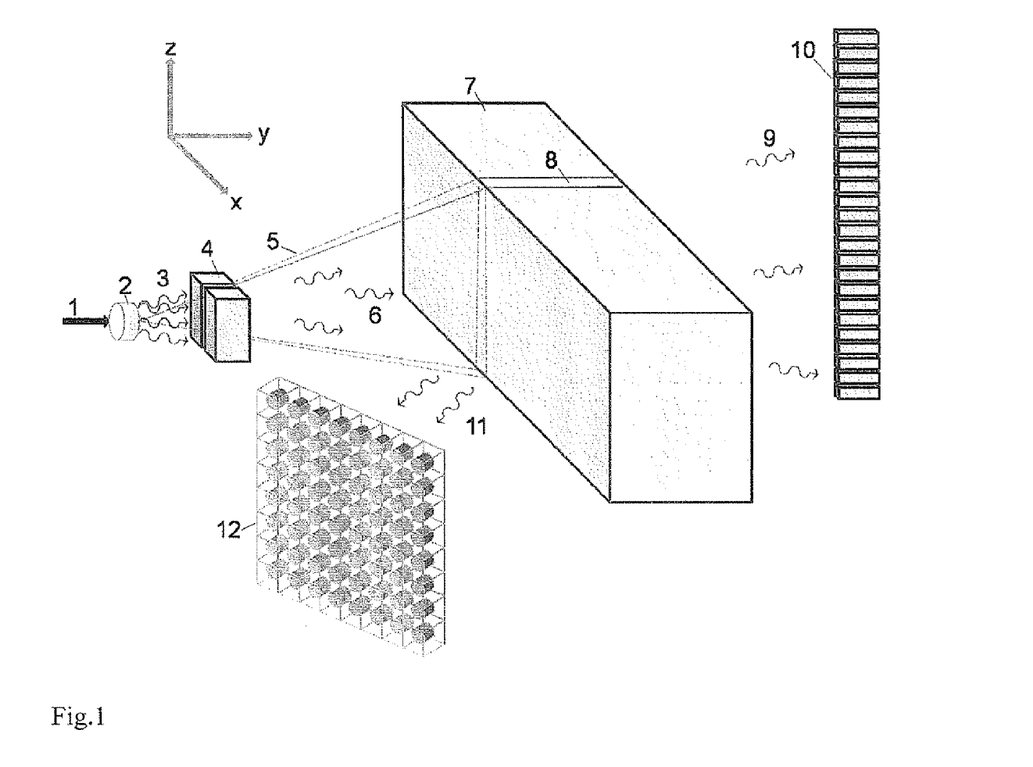
FIG. 1 is a schematic view of an article inspection device according to an embodiment of the present invention.

FIG. 1 is a schematic view of an article inspection device according to an embodiment of the present invention.

As shown in FIG. 1, in an exemplary embodiment of the present invention, the article inspection device mainly comprises an x-ray machine, a collimation unit 4, a transmission detector array 10 and a scattering detector array 12.

In this exemplary embodiment, referring to FIG. 1, the x-ray machine generates x-rays 3 by applying an electron beam 1 to bombard an electron target 2. The collimation unit 4 forms or shapes the x-rays 3 generated by the x-ray machine into a sector beam 5, and projects x-rays 6 of the sector beam 5 to an article 7. The sector beam 5 will transmit through the article 7 along a transmission cross section 8.

Also referring to FIG. 1, the transmission detector array 10 is provided at an opposite side to the x-ray machine for detecting the x-rays 9 transmitting through the article 7 so as to form a two-dimensional image of the article 7. The scattering detector array 12 is provided at an opposite side to the transmission detector array 10 for detecting scattering photons 11 from the article 7 so as to form a three-dimensional image of the article 7.

In an exemplary embodiment of the present invention, the x-ray machine, the collimation unit 4 and the transmission detector array 10 each may be a conventional one that has been applied in a traditional x-ray imaging device. For clarity, herein is omitted their further detailed description.

In an exemplary embodiment of the present invention, the electron beam 1 of the x-ray machine should have enough energy to excite the electron target 2 after the electron target 2 is bombarded by the electron beam 1 to generate the x-rays 3 having energy enough to produce an pair production effect, for example, the electron beam 1 of the x-ray machine may have energy of more than 1.022 MeV. In an exemplary embodiment of the present invention, the electron target 2 may be a composite target composed of wolfram and gold, or may be any one of conventional targets that can be adapted to the present invention.

As shown in FIG. 1, during x-rays 6 of the sector beam 5 transmit through the transmission cross section 8 of the article 7, the x-rays 6 of the sector beam 5 are attenuated because the photoelectric effect, the Compton effect, the pair production effect and the Rayleigh scattering effect occur.

In an exemplary embodiment of the present invention, referring to FIG. 1, the scattering detector array 12 is provided at the same side of the article 7 as the x-ray machine, but the scattering detector array 12 may be provided at an opposite side of the article 7 to the x-ray machine.

Figure 2:
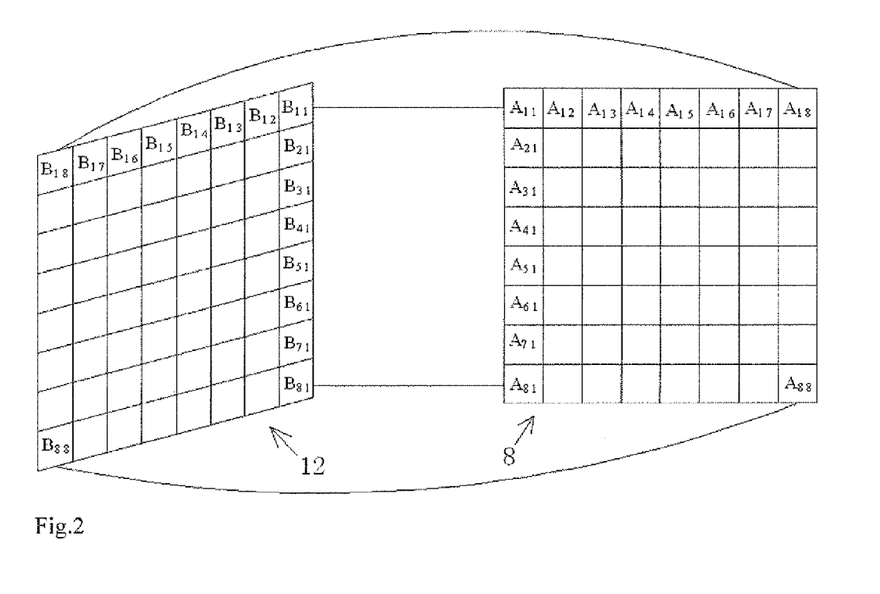
FIG. 2 is a view showing a corresponding relation between each of sub-regions of a transmission cross section of the article to be inspected and each of the scattering detector modules of the scattering detector array.

FIG. 2 shows a corresponding relation between each of sub-regions of a transmission cross section of the article and each of the scattering detector modules.

Please refer to FIG. 1 and FIG. 2, in an exemplary embodiment of the present invention, the scattering detector array 12 comprises sixty-four scattering detector modules arranged in a matrix of 8-rows and 8-columns, and all the scattering detector modules are exactly the same as one another. As shown in FIG. 2, the sixty-four scattering detector modules arranged in the matrix of 8-rows and 8-columns comprises:

Eight scattering detector modules B11-B18 in a first line of the scattering detector array 12;

Eight scattering detector modules B21-B28 in a second line of the scattering detector array 12;

Eight scattering detector modules B31-B38 in a third line of the scattering detector array 12;

Eight scattering detector modules B41-B48 in a fourth line of the scattering detector array 12;

Eight scattering detector modules B51-B58 in a fifth line of the scattering detector array 12;

Eight scattering detector modules. B61-B68 in a sixth line of the scattering detector array 12;

Eight scattering detector modules B71-B78 in a seventh line of the scattering detector array 12; and Eight scattering detector modules B81-B88 in an eighth line of the scattering detector array 12.

Similarly, please continue refer to FIG. 1 and FIG. 2, the transmission cross section 8 of the article 7 is divided into sixty-four sub-regions arranged in a matrix of 8-rows and 8-columns, and all the sub-regions are exactly the same as one another. As shown in FIG. 2, the sixty-four sub-regions arranged in the matrix of 8-rows and 8-columns comprises:

Eight sub-regions A11-A18 in a first line of the transmission cross section 8;

Eight sub-regions A21-A28 in a second line of the transmission cross section 8;

Eight sub-regions A31-A38 in a third line of the transmission cross section 8;

Eight sub-regions A41-A48 in a fourth line of the transmission cross section 8;

Eight sub-regions A51-A58 in a fifth line of the transmission cross section 8;

Eight sub-regions A61-A68 in a sixth line of the transmission cross section 8;

Eight sub-regions A71-A78 in a seventh line of the transmission cross section 8; and Eight sub-regions A81-A88 in an eighth line of the transmission cross section 8.

As shown in FIG. 2, in an exemplary embodiment of the present invention, each of the sub-regions of the transmission cross section 8 corresponds to each of the scattering detector modules of the scattering detector array 12. For example, the sub-region A11 corresponds to the scattering detector module B11; the sub-region A81 corresponds to the scattering detector module B81; the sub-region A88 corresponds to the scattering detector module B88. Thereby, in the exemplary embodiment of the present invention, each of the scattering detector modules can only detect scattering photons from the corresponding one sub-region of the transmission cross section.

Although it is not shown, in an exemplary embodiment of the present invention, the scattering detector array 12 each may comprise a plurality of same scattering detector modules arranged in a matrix of i-rows and j-columns, such as four same scattering detector modules arranged in a matrix of 2-rows and 2-columns, six same scattering detector modules arranged in a matrix of 2-rows and 3-columns, six same scattering detector modules arranged in a matrix of 3-rows and 2-columns, nine same scattering detector modules arranged in a matrix of 3-rows and 3-columns, twelve same scattering detector modules arranged in a matrix of 3-rows and 4-columns, and so on. That is, in the exemplary embodiment of the present invention, 'i' may be a positive integer equal to or greater than 2, and 'j' may be a positive integer equal to or greater than 2. Similarly, the transmission cross section 8 may be divided into a plurality of same sub-regions arranged in a matrix of i-rows and j-columns.

In the exemplary embodiment of the present invention, the resolution of the three-dimensional image formed by the article inspection device is proportional to parameters 'i' and 'j'. That is, when the parameters 'i' and 'j' become larger, the resolution of the three-dimensional image becomes higher. But the parameters and 'j' can not be too large, otherwise it makes the cost of the article inspection device very high.

Figure 3:
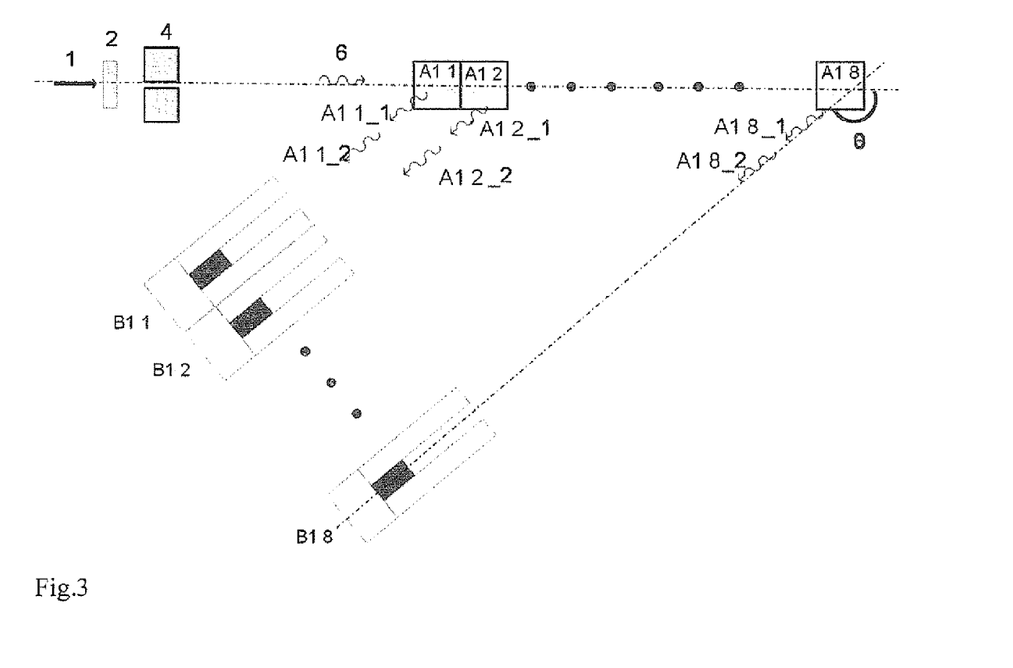
FIG. 3 is a cross section view along a plane perpendicular to Z-axis shown in FIG. 1.

FIG. 3 is a cross section view along a plane perpendicular to Z-axis shown in FIG. 1. Next the procedure of detecting scattering photons generated at respective sub-regions by using respective scattering detector modules will be described with respect to FIG. 3.

As above description, during the x-rays 6 of the sector beam 5 transmit through the transmission cross section 8 of the article 7, the photoelectric effect, the Compton effect, the pair production effect and the Rayleigh scattering effect. The four effects will be simply described as follows.

1) Photoelectric Effect

In the photoelectric effect, photons are absorbed and their energy is converted into the energy of photoelectrons and characteristic x-rays. Generally, the photoelectrons can not be detected by the scattering detector modules, and the characteristic x-rays do not have enough energy to pass through the article and thus can not be detected by the scattering detector modules. But because of bremsstrahlung effect, the photoelectrons may be converted into x-rays having high energy and thus can be detected by the scattering detector modules.

However, the present invention takes no interest in x-rays entering the scattering detector modules at all.

2) Compton Effect

As shown in FIG. 3, when incident x-rays 6 react with respective sub-regions of the transmission cross section 8 of the article 7, the Compton Effect may occur.

Please refer to FIG. 3, when the incident x-rays 6 react with the sub-region A11, the Compton-effect scattering photons A11_1 may enter a scattering detector of a scattering detector module B11. In an exemplary embodiment of the present invention, the scattering detector module B11 is designed and arranged so that only the Compton-effect scattering photons A11_1 from the sub-region A11 corresponding to the scattering detector module B11 can enter the scattering detector module B11. Similarly, any one of other scattering detector modules B12-B18 is also designed and arranged to only receive the Compton-effect scattering photons from one sub-region corresponding to it. For example, as shown in FIG. 3, the scattering detector module B12 can only receive the Compton-effect scattering photons A12_1 from the sub-region A12 . . . , the scattering detector module B18 can only receive the Compton-effect scattering photons A18_1 from the sub-region A18.

It is well known that the Compton scattering cross section is proportional to the atomic number when the energy of the incident x-rays 6 is constant. Therefore, in case respective sub-regions of the article have a same atomic density, the larger is the atomic number of one sub-region of the article, the larger is the Compton-effect scattering photon count detected by a scattering detector module corresponding to the one sub-region.

3) Pair Production Effect

As shown in FIG. 3, when the incident x-rays 6 react with respective sub-regions of the transmission cross section 8 of the article 7, the pair production effect may occur. In the pair production effect, because flight in a solid of positron produced by the pair production effect is in the order of millimeter, each positron is annihilated and finally becomes two gamma photons each having energy of 511 KeV, the position where the two gamma photons are produced is in the sub-region A11.

Please refer to FIG. 3, in an exemplary embodiment of the present invention, the scattering detector module B11 is designed and arranged so that only the pair production effect annihilation photons A11_2 from a sub-region A11 corresponding to the scattering detector module B11 can enter the scattering detector module B11. Similarly, any one of the other scattering detector modules B12-B18 is also designed and arranged to only receive the pair production effect annihilation photons from one sub-region corresponding to it. For example, as shown in FIG. 3, the scattering detector module B12 can only receive the pair production effect annihilation photons A12_2 from the sub-region A12 . . . , the scattering detector module B18 can only receive the pair production effect annihilation photons A18_2 from the sub-region A18.

It is well known that the pair production effect cross section is proportional to the second power of the atomic number. Therefore, in case respective sub-regions of the article have a same atomic density, the larger is the atomic number of one sub-region of the article, the larger is the pair production effect annihilation photon count detected by a scattering detector module corresponding to the one sub-region.

4) Rayleigh Scattering Effect

When the incident x-rays 6 have energy of more than 1.022 MeV, the Rayleigh scattering effect can be omitted because Rayleigh scattering cross section is very small.

Among the above four scattering effects, the scattering detector array 12 takes interest in only the Compton scattering effect and the pair production effect. As the above description, the Compton-effect scattering photon count and the pair production effect annihilation photon count are proportional to the first power and the second power of the atomic number, respectively. Therefore, the ratio of the pair production effect annihilation photon count detected by scattering detector array 12 to the Compton-effect scattering photon count detected by scattering detector array 12 is proportional to the first power of the atomic number. Accordingly, the atomic number information of respective sub-regions of the article can be obtained by the ratio of the pair production effect annihilation photon count to the Compton-effect scattering photon count.

Figure 4:
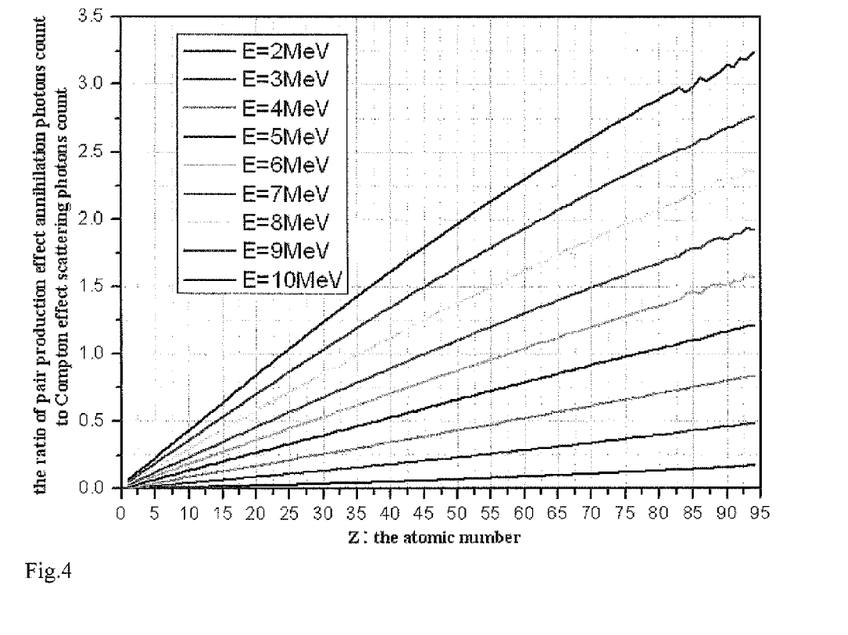
FIG. 4 shows a relation between an atomic number and a ratio of the pair production effect annihilation photon count to the Compton-effect scattering photon count.

FIG. 4 shows a relation between the ratio of the pair production effect annihilation photon count to the Compton-effect scattering photon count and the atomic number when incident x-rays 6 have different energies.

Referring to FIG. 4, there is an excellent linear relationship between the ratio of the pair production effect annihilation photon count to the Compton-effect scattering photon count and the atomic number. Therefore, the atomic number can be calculated by a following formula:

$$Z_{pc} = \frac{C_{-pair}}{C_{-compton}} \propto Z.$$

Wherein, $C_{-pair}$ is the pair production effect annihilation photon count;

$C_{-compton}$ is the Compton-effect scattering photon count;

$Z_{pc}$ is the ratio of the pair production effect annihilation photon count to the Compton-effect scattering photon count;

Z is the atomic number.

In practice, because of some unavoidable errors, it is necessary to calibrate the relation between the ratio Zpc and the atomic number Z according to experiments.

As the above description, the transmission cross section 8 of the article 7 is divided into a plurality of same sub-regions arranged in a matrix of i-rows and j-columns, and the scattering detector array 12 each correspondingly comprises a plurality of same scattering detector modules arranged in a matrix of i-rows and j-columns. Thereby, the atomic numbers at all sub-regions, arranged in a matrix of i-rows and j-columns, of the transmission cross section 8 can be obtained by the detection information from the scattering detector modules, arranged in a matrix of i-rows and j-columns, of the scattering detector array 12. When the article is wholly scanned, the atomic numbers at every sub-region of every transmission cross section 8 of the article can be obtained, and then a three-dimensional image of the whole article can be formed according to the atomic numbers at every sub-region of every transmission cross section 8 of the article.

Figure 5:
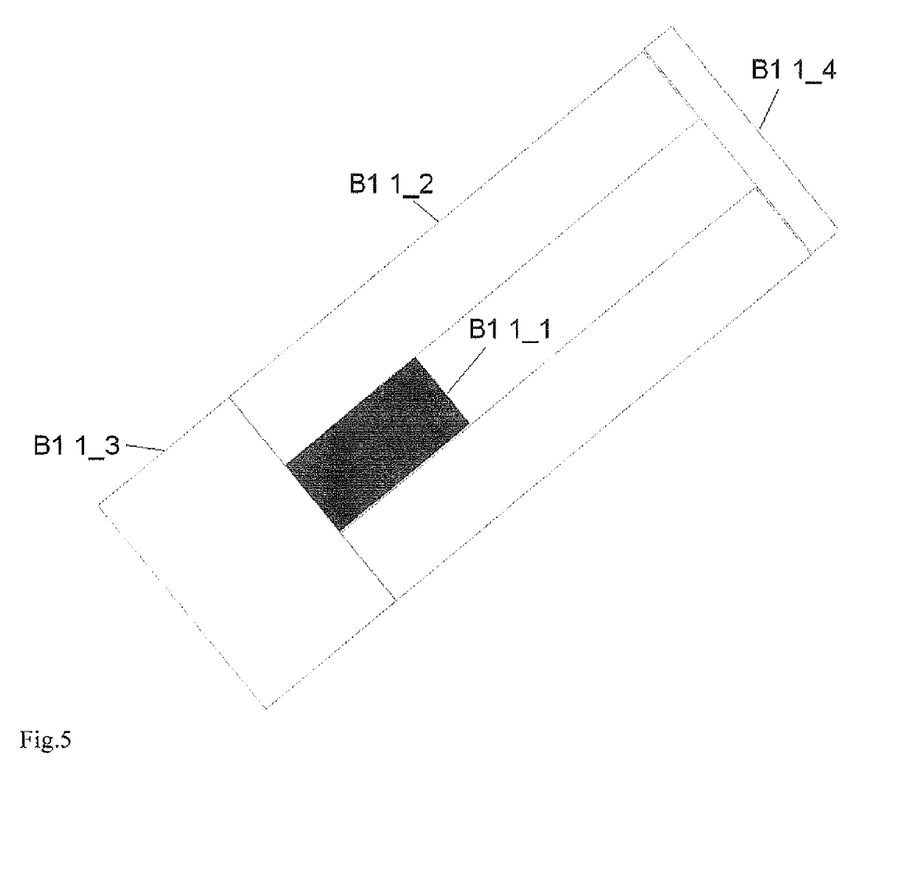
FIG. 5 is a schematic structure view of each of scattering detector modules of the scattering detector array.

FIG. 5 is a schematic structure view of each of scattering detector modules of the scattering detector array.

In an exemplary embodiment of the present invention, since each of the scattering detector modules of the scattering detector array 12 is exactly the same as one another, herein will only describe the scattering detector module B11 corresponding to the sub-region A11, as shown in FIG. 5.

Please refer to FIG. 3 and FIG. 5, the scattering detector module B11 comprises a detector B11_1 and a collimator B11_2. In the illustrated exemplary embodiment, the collimator B11_2 is configured to permit only the pair production effect annihilation photons A11_2 and the Compton effect scattered photons A11_1 from the sub-region A11 corresponding to the collimator B11_2 to enter the detector B11_1, that is, the collimator B11_2 is configured to substantially absorb the pair production effect annihilation photons and the Compton effect scattered photons from other sub-regions not corresponding to the collimator B11_2.

In an exemplary embodiment of the present invention, the detector B11_1 may be a type of detector with a high energy resolution and a quick time response characteristic.

In an exemplary embodiment of the present invention, the detector B11_1 may be a plastic scintillator detector or a liquid scintillator detector. The plastic scintillator detector and the liquid scintillator detector both have a quick time response characteristic and can detect the gamma photons within nanoseconds.

In an exemplary embodiment of the present invention, the detector B11_1 may be a $LaBr_3(Ce)$ detector or a $LaCl_3(Ce)$ detector. The $LaBr_3(Ce)$ detector and the $LaCl_3(Ce)$ detector both have a high energy resolution and a quick time response characteristic.

In an exemplary embodiment of the present invention, the detector B11_1 may be an HPGe detector. The HPGe detector has en excellent energy resolution, but has a poor time response characteristic.

In an exemplary embodiment of the present invention, the detector B11_1 may be a CdZnTe detector. The CdZnTe detector also has an excellent energy resolution, but has a poor time response characteristic and its price is very high.

In an exemplary embodiment of the present invention, the collimator B11_2 may be made of lead, steel or copper. In this way, the collimator B11_2 may effectively absorb the pair production effect annihilation photons and the Compton effect scattered photons from other sub-regions not corresponding to it, and permits only the pair production effect annihilation photons and the Compton effect scattered photons from the sub-region A11 corresponding to it to enter its detector.

In an exemplary embodiment of the present invention, as shown in FIG. 3 and FIG. 5, the scattering detector module B11 further comprises a shield B11_3 for preventing the pair production effect annihilation photons A11_2 and the Compton effect scattered photons A11_1 from sub-regions not corresponding to the scattering detector module B11 from entering the detector B11_1, and particularly, preventing various transmitting or scattering x-rays from the electron target 2 from entering the detector B11_1. In an exemplary embodiment of the present invention, the shield B11_3 may be made of lead, steel or copper, or other suitable material.

In an exemplary embodiment of the present invention, as shown in FIG. 3 and FIG. 5, the scattering detector module B11 further comprises a hardenite B11_4 for decreasing the intensity of the pair production effect annihilation photons A11_2 and the Compton effect scattered photons A11_1 from the sub-region A11 corresponding to the scattering detector module B11 so as to decrease the intensity of the pair production effect annihilation photons A11_2 and the Compton effect scattered photons A11_1 entering the detector B11_1. Otherwise, the detector B11_1 may be in an abnormal operation state because the counting rate is too high. In an exemplary embodiment of the present invention, the hardenite B11_4 may be made of lead, steel or copper, or other suitable material.

Please continue refer to FIG. 5, in an exemplary embodiment of the present invention, the detector B11_1 is located in a collimation slit of the collimator B11_2. The shield B11_3 is disposed at one side of the collimator B11_2 opposite to the hardenite B11_4 and seals an opening of the collimation slit at the one side. The hardenite B11_4 is disposed at the other side of the collimator B11_2, and seals the other opening of the collimation slit at the other side.

In an exemplary embodiment of the present invention, the shield B11_3 and the collimator B11_2 are formed into a piece. But please be noted that the shield B11_3 and the collimator B11_2 may be formed into two individual pieces.

Figure 6:
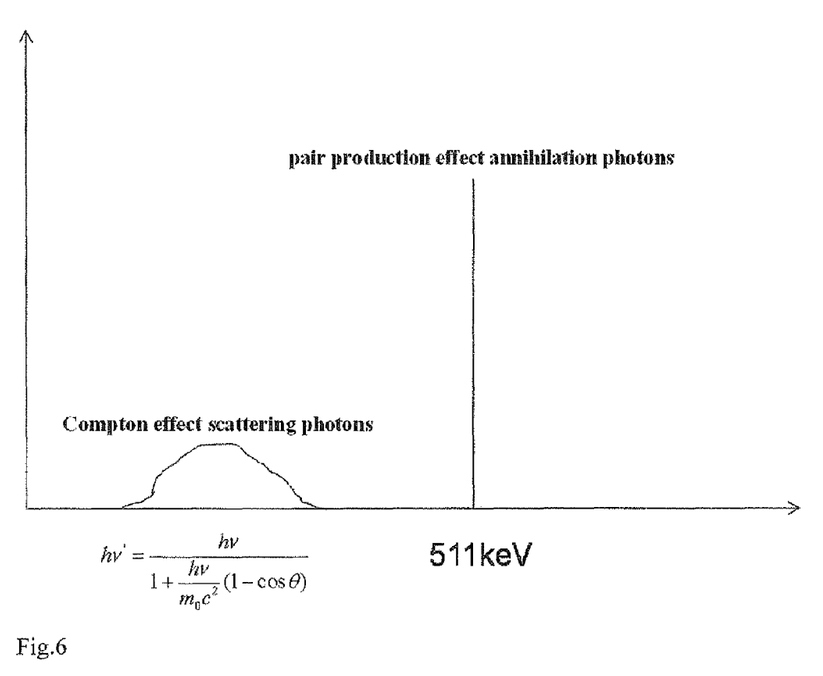
FIG. 6 shows energy spectrums of the pair production effect annihilation photons and the Compton-effect scattering photons entering the scattering detector arrays.

FIG. 6 shows energy spectrums of the pair production effect annihilation photons and the Compton effect scattered photons entering the scattering detector array 12.

As shown in FIG. 6, the pair production effect annihilation photons have energy of 511 KeV.

As a formula shown in FIG. 6, the energy of the Compton-effect scattering photons is mainly related to two parameters: Compton scattering angle θ (please see FIG. 3) and the energy hv of the incident x-rays 6. Because the energy spectrum of the incident x-rays 6 is a continuous energy spectrum, the energy spectrum of the Compton-effect scattering photons is also a continuous energy spectrum, as shown in FIG. 6.

Although several exemplary embodiments have been shown and described, it would be appreciated by those skilled in the art that various changes or modifications may be made in these embodiments without departing from the principles and spirit of the disclosure, the scope of which is defined in the claims and their equivalents.

What is claimed is:

1. An article inspection device, comprising:
   a x-ray machine;
   a collimation unit for shaping x-rays generated by the x-ray machine into a sector beam to project an article;
   a transmission detector array for detecting the x-rays transmitting through the article so as to form a two-dimensional image of the article; and
   a scattering detector array comprising a plurality of same scattering detector modules arranged in a matrix of i-rows and j-columns,
   wherein a transmission cross section of the article transmitted by the x-rays is divided into a plurality of same sub-regions arranged in a matrix of i-rows and j-columns,
   wherein the plurality of scattering detector modules arranged in i-rows and j-columns correspond to the plurality of sub-regions arranged in i-rows and j-columns one by one for detecting pair production effect annihilation photons and Compton-effect scattering photons from the respective sub-regions produced by the x-rays,
   wherein obtaining atomic numbers of the respective sub-regions based on a ratio of the pair production effect annihilation photon count to the Compton-effect scattering photon count, so as to form a three-dimensional image of the article,
   wherein 'i' is a positive integer equal to or greater than 2, and 'j' is a positive integer equal to or greater than 2.

2. The article inspection device according to claim 1, wherein each of the scattering detector modules comprises:
   a detector; and
   a collimator for absorbing the pair production effect annihilation photons and the Compton-effect scattering photons from other sub-regions not corresponding to the collimator to permit only the pair production effect annihilation photons and the Compton-effect scattering photons from the one sub-region corresponding to the collimator to enter the detector.

3. The article inspection device according to claim 2, wherein the detector is a $LaBr_3(Ce)$ detector, a $LaCl_3(Ce)$ detector, a HPGe detector or a CdZnTe detector.

4. The article inspection device according to claim 2, wherein the collimator is made of lead, steel or copper.

5. The article inspection device according to claim 2, wherein each of the scattering detector modules further comprises:
a shield for preventing the pair production effect annihilation photons and the Compton-effect scattering photons, from sub-regions not corresponding to the collimator of the scattering detector module, from entering the detector.

6. The article inspection device according to claim 5, wherein the shield is made of lead, steel or copper.

7. The article inspection device according to claim 5, wherein each of the scattering detector modules further comprises:
a hardenite for decreasing the intensity of the pair production effect annihilation photons and the Compton-effect scattering photons from the one sub-region corresponding to the collimator of the scattering detector module.

8. The article inspection device according to claim 7, wherein the hardenite is made of lead, steel or copper.

9. The article inspection device according to claim 7, wherein
the detector is located in a collimation slit of the collimator;
the shield is disposed at one side of the collimator opposite to the article, and seals an opening of the collimation slit at the one side; and
the hardenite is disposed at the other side of the collimator facing the article, and seals the other opening of the collimation slit at the other side.

10. The article inspection device according to claim 9, wherein the shield and the collimator are formed into a piece.

11. The article inspection device according to claim 1, wherein the x-ray machine is a monoenergetic x-ray machine or a polyenergetic x-ray machine.

12. The article inspection device according to claim 1, wherein the x-rays generated by the x-ray machine have energy of more than 1.022 MeV.

13. A method for inspecting an article by using article inspection device according to claim 1, comprising:
detecting an attenuation information of x-rays transmitting through an article by use of a transmission detector array, and detecting pair production effect annihilation photon count and Compton-effect scattering photon count during the x-rays transmits through the article by use of scattering detector array; and
forming a two-dimensional image of the article based on the detected attenuation information, and forming a three-dimensional image of the article based on a ratio of the pair production effect annihilation photon count to the Compton-effect scattering photon count.

* * * * *